US010960074B2

(12) United States Patent
Berdahl (10) Patent No.: US 10,960,074 B2
(45) Date of Patent: Mar. 30, 2021

(54) PROCESS FOR TREATING GLAUCOMA (71) Applicant: John Berdahl, Sioux Falls, SD (US)

(72) Inventor: John Berdahl, Sioux Falls, SD (US)

(73) Assignee: John Berdahl, Sioux Falls, SD (US)

( * ) Notice: Subject to any disclaimer, the term of this patent is extended or adjusted under 35 U.S.C. 154(b) by 463 days.

(21) Appl. No.: 16/018,670

(22) Filed: Jun. 26, 2018

(65) Prior Publication Data

US 2018/0303938 A1    Oct. 25, 2018

Related U.S. Application Data

(63) Continuation of application No. 14/877,499, filed on Oct. 7, 2015, now Pat. No. 10,029,009, which is a continuation of application No. 12/380,239, filed on Feb. 25, 2009, now Pat. No. 9,168,172.

(51) Int. Cl.
*A61K 45/00*    (2006.01)
*A61F 9/007*    (2006.01)
*A61M 27/00*    (2006.01)

(52) U.S. Cl.
CPC .......... *A61K 45/00* (2013.01); *A61F 9/00781* (2013.01); *A61M 27/006* (2013.01); *A61M 27/002* (2013.01)

(58) Field of Classification Search
CPC .. A61F 9/00781; A61K 45/00; A61M 27/002; A61M 27/006; A61B 5/031
See application file for complete search history.

(56) References Cited

U.S. PATENT DOCUMENTS

| 4,604,087 | A |   | 8/1986  | Joseph et al.    |            |
|-----------|---|---|---------|------------------|------------|
| 5,300,020 | A |   | 4/1994  | L'Esperance, Jr. |            |
| 5,338,291 | A |   | 8/1994  | Speckman et al.  |            |
| 6,129,682 | A |   | 10/2000 | Borchert et al.  |            |
| 6,162,428 | A | * | 12/2000 | Snable ..........  | A61K 35/30 |
|           |   |   |         |                  | 424/93.1   |
| 7,850,638 | B2|   | 12/2010 | Theodore         |            |

(Continued)

OTHER PUBLICATIONS

Morgan et al., "The influence of cerebrospinal fluid pressure on the lamina cribosa tissue pressure gradient," Invest Ophthalmol Vis Sci. 1995; 36: 1163-1172 (abstract only).*

(Continued)

*Primary Examiner* — Susan S Su
(74) *Attorney, Agent, or Firm* — Schwegman Lundberg & Woessner, P.A.

(57) ABSTRACT

A process for treating glaucoma whereby the treatment can be accomplished by the use of medication or by surgery, or both, in order to control or prevent the occurrence of glaucoma. The optic nerve is aligned within and between two distinct pressurized spaces and within the dural sheath, the intraocular space and the intracranial space having an intraocular pressure (IOP) and an intracranial pressure (ICP), respectively. Medicine can be administered to raise the intracranial pressure in order to reach a desirable lower translaminar pressure difference across these two pressurized spaces which are separated by the lamina cribrosa in order to treat glaucoma. An alternate closely related mode of the treatment process is the implanting of a shunt substantially between the intraocular space and the intracranial space in order to beneficially equalize pressure differentials across the intraocular space and the intracranial space.

19 Claims, 5 Drawing Sheets

(56) References Cited

U.S. PATENT DOCUMENTS

| | | | |
|---|---|---|---|
| 8,408,204 B2 | 4/2013 | Lurie | |
| 9,168,172 B1 | 10/2015 | Berdahl | |
| 10,029,009 B1 | 7/2018 | Berdahl | |
| 2003/0199574 A1* | 10/2003 | Karageozian | A61K 31/155 514/468 |
| 2004/0202677 A1* | 10/2004 | Hopkins | A61K 36/04 424/195.17 |
| 2004/0254517 A1 | 12/2004 | Quiroz-Mercado et al. | |
| 2008/0306429 A1 | 12/2008 | Shields et al. | |
| 2013/0274638 A1 | 10/2013 | Jennings et al. | |
| 2017/0188860 A1 | 7/2017 | Fuller et al. | |
| 2018/0228970 A1* | 8/2018 | Wostyn | A61M 27/006 |

OTHER PUBLICATIONS

Wostyn, Peter, et al., "Intracranial pressure and glaucoma:Is there a new therapeutic perspective on the horizon?", Medical Hypotheses 118 (2018)98-102, (2018), 5 pgs.

"U.S. Appl. No. 12/380,239, Amendment filed May 8, 2014", 11 pgs.

"U.S. Appl. No. 12/380,239, Corrected Notice of Allowance dated Jul. 8, 2015", 3 pgs.

"U.S. Appl. No. 12/380,239, Final Office Action dated Oct. 8, 2014", 12 pgs.

"U.S. Appl. No. 12/380,239, Non Final Office Action dated Feb. 6, 2015", 9 pgs.

"U.S. Appl. No. 12/380,239, Non Final Office Action dated Jul. 14, 2011", 15 pgs.

"U.S. Appl. No. 12/380,239, Notice of Allowance dated Jun. 19, 2015", 5 pgs.

"U.S. Appl. No. 12/380,239, Notice of Non-Compliant Amendment dated Jun. 20, 2014", 2 pgs.

"U.S. Appl. No. 12/380,239, Response filed Jan. 7, 2015 to Final Office Action dated Oct. 8, 2014", 20 pgs.

"U.S. Appl. No. 12/380,239, Response filed Apr. 16, 2014 to Non Final Office Action dated Jul. 14, 2011", 12 pgs.

"U.S. Appl. No. 12/380,239, Response filed May 4, 2015 to Non Final Office Action dated Feb. 6, 2015", 13 pgs.

"U.S. Appl. No. 12/380,239, Response filed Jul. 1, 2011 to Restriction Requirement dated Jun. 2, 2011", 3 pgs.

"U.S. Appl. No. 12/380,239, Response filed Oct. 12, 2012 to Non Final Office Action dated Jul. 14, 2011", 12 pgs.

"U.S. Appl. No. 12/380,239, Response to Notice of Non-Compliant Amendment dated Jun. 24, 2014", 14 pgs.

"U.S. Appl. No. 12/380,239, Restriction Requirement dated Jun. 2, 2011", 5 pgs.

"U.S. Appl. No. 14/877,499, Non Final Office Action dated Nov. 27, 2017", 7 pgs.

"U.S. Appl. No. 14/877,499, Notice of Allowance dated Mar. 30, 2018", 5 pgs.

"U.S. Appl. No. 14/877,499, Preliminary Amendment filed Oct. 8, 2015", 5 pgs.

"U.S. Appl. No. 14/877,499, Response filed Feb. 14, 2018 to Non Final Office Action dated Nov. 27, 2017", 7 pgs.

Berdahl, et al., "Cerebrospinal fluid pressure is decreased in primary open-angle glaucoma", Ophthalmology 115(5), (May 2008), 763-768.

Chowdhury, et al., "Intracranial Pressure and Its Relationship to Glaucoma: Current Understanding and Future Directions", Med Hypothesis Discov Innov Ophthalmol, 4(3), (2015), 1 pg.

Digre, Kathleen, "Not so benign intracranial hypertension", MBJ, 326(7390), (Mar. 22, 2003), 613-614.

Hillen, Mark, "In Practice (VIIP: A Space Odyssey)", The Ophthalmologist, vol. 11, (Sep. 2014), 6 pgs.

Jonas, Jost B., et al., "Anatomic Relationship between Lamina Cribosa, Intraocular Space, and Cerebrospinal Fluid Space", Investigative Ophthalmology & Visual Science, vol. 44, No. 12, (Dec. 2003), 5189-5195.

Kwon, et al., "A Patient's Guide to Glaucoma", sections 5A and 6B, (2006), 4 pgs.

Lehman, et al., "Experimental effect of intracranial hypertension upon intraocular pressure", J Neurosurg, 36(1):60-6, (Jan. 1972), 1 pg.

Parsa, C F, "Spontaneous venous pulsations should be monitored during glaucoma therapy", Br J Ophthalmol, 86(10), (Oct. 2002), 1187.

Sajjadi, et al., "The Relation between Intracranial and Intraocular Pressures: Study of 50 Patients", Ann Neurol, (2006), 867-870.

Samuelson, T W, "Intracranial pressure may play significant role in glaucoma", Ocular Surgery News US Edition, (Oct. 25, 2008), 3 pgs.

\* cited by examiner

PROCESS FOR TREATING GLAUCOMA

CROSS REFERENCES TO RELATED APPLICATIONS

This application is a continuation of U.S. patent application Ser. No. 14/877,499 filed Oct. 7, 2015 which claims the benefit of priority to U.S. patent application Ser. No. 12/380,239, filed Feb. 25, 2009, all of which are hereby incorporated by reference herein in their entirety and the benefit of priority of each of which is hereby claimed.

BACKGROUND OF THE INVENTION

The present invention is used in the field of medicine and, more particularly, can be used in ophthalmology as a process for the treatment of glaucoma.

DESCRIPTION OF THE PRIOR ART

Glaucoma, the second leading cause of blindness worldwide, is an optic neuropathy associated with damage to the optic nerve and visual field loss. The damage caused to the optic nerve by glaucoma is generally accepted to be irreversible. The exact causes and mechanisms that cause glaucoma are substantially heretofore unknown; however, high intraocular pressure is the most important risk factor in the manifestation of glaucoma. One known treatment for glaucoma is lowering the intraocular pressure either by surgery or by the use of medications. The surgical approach has numerous complications and often both surgery and/or medications fail to lower the intraocular pressure adequately.

SUMMARY OF THE INVENTION

The general purpose of the present invention is to provide a process for treating glaucoma. Glaucoma is an optic neuropathy that has traditionally been considered a disease isolated to the eye and associated with a high intraocular pressure primary mechanism where treatment can be accomplished by surgery or by the use of medication in order to reduce or otherwise modify such high intraocular pressure (IOP). As disclosed and indicated in a study entitled "Intracranial Pressure in Primary Open Angle Glaucoma, Normal Tension Glaucoma, and Ocular Hypertension: A Case Control Study", published Aug. 21, 2008, co-authored by the inventor, and as disclosed in a study entitled "Cerebrospinal Fluid Pressure is Decreased in Primary Open-angle Glaucoma", by Berdahl et al. in *Ophthalmology*, Volume 115, Number 5, May 2008, another primary mechanism of glaucoma is closely related to and associated with low intracranial pressure (ICP). The recent study indicates that a low intracranial pressure, referenced by the measurement of cerebrospinal fluid pressure by a spinal tap, is strongly associated with and possibly causative of glaucoma and further indicates that elevated intracranial pressure is protective of glaucoma. Ideally and in a perfect situation, increasing intracranial pressure either surgically or medically could be beneficial in the treatment of existing glaucoma and to prevent glaucoma from occurring in high risk individuals. Raising intracranial pressure (ICP) would be able to prevent blindness from or progression of glaucoma and, in addition, raising intracranial pressure would be able to prevent glaucoma from occurring.

Further, and more practically, procedures and teachings of the present invention can accomplish treatment of glaucoma in one or more fashions with respect to the features and functions of the eye and closely associated parts thereof. The optic nerve traverses two distinct pressurized spaces within the dural sheath, the intraocular space and the intracranial space having intraocular pressure (IOP) and an intracranial pressure (ICP), respectively. The critical issue relating to glaucoma is the pressure difference relationship between the intracranial pressure and the intraocular pressure. These two pressurized spaces are separated by the lamina cribrosa and the pressure difference across the lamina cribrosa is described as the translaminar pressure difference (Mathematically expressed as: Translaminar Pressure Difference=Intraocular Pressure−Intracranial Pressure). By reducing the translaminar pressure difference either by lowering intraocular pressure or by raising intracranial pressure by one or more ways, including the use of medicines, performing surgery, or both, the forces generated at the optic nerve head by pressure can be minimized and thus damage to the optic nerve can be minimized.

One treatment of glaucoma by the present invention can be accomplished by the use of an orally or intravenously administered medication to selectively raise intracranial pressure to increase cerebrospinal fluid (CSF) production through stimulation of the choroid plexus (where cerebrospinal fluid is produced) or to decrease cerebrospinal fluid reabsorbtion by inactivating the arachnoid granulations. Ideally, the ultimate goal for the treatment of glaucoma or for the prevention of glaucoma would be to make the pressure difference across the lamina cribrosa, the structure that separates the optic nerve into intraocular and intracranial components, zero; however, in practice, such pressure modification may be difficult to accomplish but can be treated by orally or intravenously administering medication to bring pressures and differentials thereof into beneficial and acceptable values and ranges. For purposes of example and demonstration, the average intraocular pressure (IOP) is 16 mm Hg with a normal range of 10-21 mm Hg and the average intracranial pressure (ICP) is about 12 mm Hg with a normal range of 5-20 mm Hg. Preferably, if the translaminar pressure difference (IOP−ICP) is less than 6 mm Hg, glaucoma will not occur. If the translaminar pressure difference (IOP−ICP) is between 6-10 mm Hg, a person is at risk for developing glaucoma. If the translaminar pressure difference (IOP−ICP) is equal to or greater than 10 mm Hg, a person is at high risk and will likely develop glaucoma. Thus, orally or intravenously administered medication can be used in order to bring the translaminar pressure difference (IOP−ICP) to less than 6 mm Hg, wherein glaucoma will not occur. In the alternative, orally or intravenously administered medication can be used to lower a high translaminar pressure difference closer to, but not within, the suitable translaminar pressure difference (IOP−ICP) of between 6-10 mm Hg and combined with the current surgical practice of lowering the intraocular pressure to adequately decrease the translaminar pressure difference. Raising intracranial pressure by orally or intravenously administering medication by itself or in combination with surgical intraocular pressure lowering procedures may adequately decrease the translaminar pressure difference to a suitable value and arrest or prevent glaucoma. With respect to a surgical solution, a shunt could be placed from the anterior chamber of the eye into the subarachnoid space surrounding the optic nerve. This shunt would divert aqueous humor into the subarachnoid space which is typically occupied by cerebrospinal fluid and in fluid communication with the inner cranial space, where an inner cranial pressure is present, preferably at an elevated vale. This would accomplish the ultimate goal of equalizing the translaminar pressure difference.

The surgical treatment of glaucoma includes the use of a surgically implanted tubular shunt of flexible silicone or other suitable material, the proximal end of the tubular shunt is placed in the anterior chamber of the eye. The shunt extends exterior to the eye's sclera where the shunt distal end terminates within the subarachnoid space surrounding the optic nerve and which space is typically occupied by cerebrospinal fluid. The tubular shunt diverts the higher pressure aqueous humor fluid via the subarachnoid space to the intracranial space, thereby equalizing the translaminar pressure gradient wherein the translaminar pressure difference (IOP–ICP) is less than the 6-10 mm Hg risk range and less than the high risk range equal to or greater than 10 mm Hk. Preferably, after the surgical treatment by the use of this invention, the translaminar pressure difference is equalized at zero translaminar pressure difference. The installation and use of the shunt accomplishes the ultimate goal of equalizing the translaminar pressure difference in order to treat or prevent the occurrence of glaucoma.

According to one or more embodiments of the present invention, there is provided a process for of treating glaucoma involving the modification of pressures associated with the eye by the administration of medications and/or by the use of surgery to implant a device.

One significant aspect and feature of the present invention is a process for treating or preventing glaucoma.

Another significant aspect and feature of the present invention is the treatment or prevention of glaucoma by the use of medicines.

Another significant aspect and feature of the present invention is the treatment or prevention of glaucoma by the use of surgery.

Still another significant aspect and feature of the present invention is the use of medicine to elevate intracranial pressure in order to treat or prevent glaucoma.

Still another significant aspect and feature of the present invention is the use of medicine to selectively elevate intracranial pressure by increasing cerebrospinal fluid (CSF) production through stimulation of the choroid plexus in order to treat or prevent glaucoma.

Still another significant aspect and feature of the present invention is the use of medicine to selectively elevate intracranial pressure by decreasing cerebrospinal fluid reabsorbtion by inactivating the arachnoid granulations in order to treat or prevent glaucoma.

Still another significant aspect and feature of the present invention is the use of medicine to reduce the pressure differential across the lamina cribrosa in order to treat glaucoma.

Still another significant aspect and feature of the present invention is the use of medicine to reduce translaminar pressure difference (IOP–ICP) in order to treat or prevent glaucoma.

Still another significant aspect and feature of the present invention is the use of medicine to provide translaminar pressure difference (IOP–ICP) less than 6 mm Hg in order to treat or prevent glaucoma.

Yet another significant aspect and feature of the present invention is the use of surgery to lower the intraocular pressure combined with a medicinal treatment to elevate the intracranial pressure in order to provide for a suitable reduction of translaminar pressure difference (IOP–ICP) and thus to treat or prevent glaucoma.

Still another significant aspect and feature of the present invention is the use of a shunt communicating with and extending from the anterior chamber of the eye along the outer portion of the sclera and then through the dural sheath and into and communicating with the subarachnoid and intracranial space.

Still another significant aspect and feature of the present invention is the use of a shunt to equalize intraocular pressure (IOP) and intracranial pressure (ICP), thus realizing a beneficial translaminar pressure difference (IOP–ICP) of zero.

Still another significant aspect and feature of the present invention is the use of a shunt having a plurality of holes at the distal end.

Still another significant aspect and feature of the present invention is the use of a shunt having a distally located anchor barb.

Still another significant aspect and feature of the present invention is the use of an anchoring ring at the distal end of a shunt.

Still another significant aspect and feature of the present invention is the use of an anchoring barb and an anchoring ring to affix the position of the distal end of the shunt within the subarachnoid space.

Having thus described embodiments of the present invention and having set forth significant aspects and features of the present invention, it is the principal object of the present invention to provide a process for treating glaucoma.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
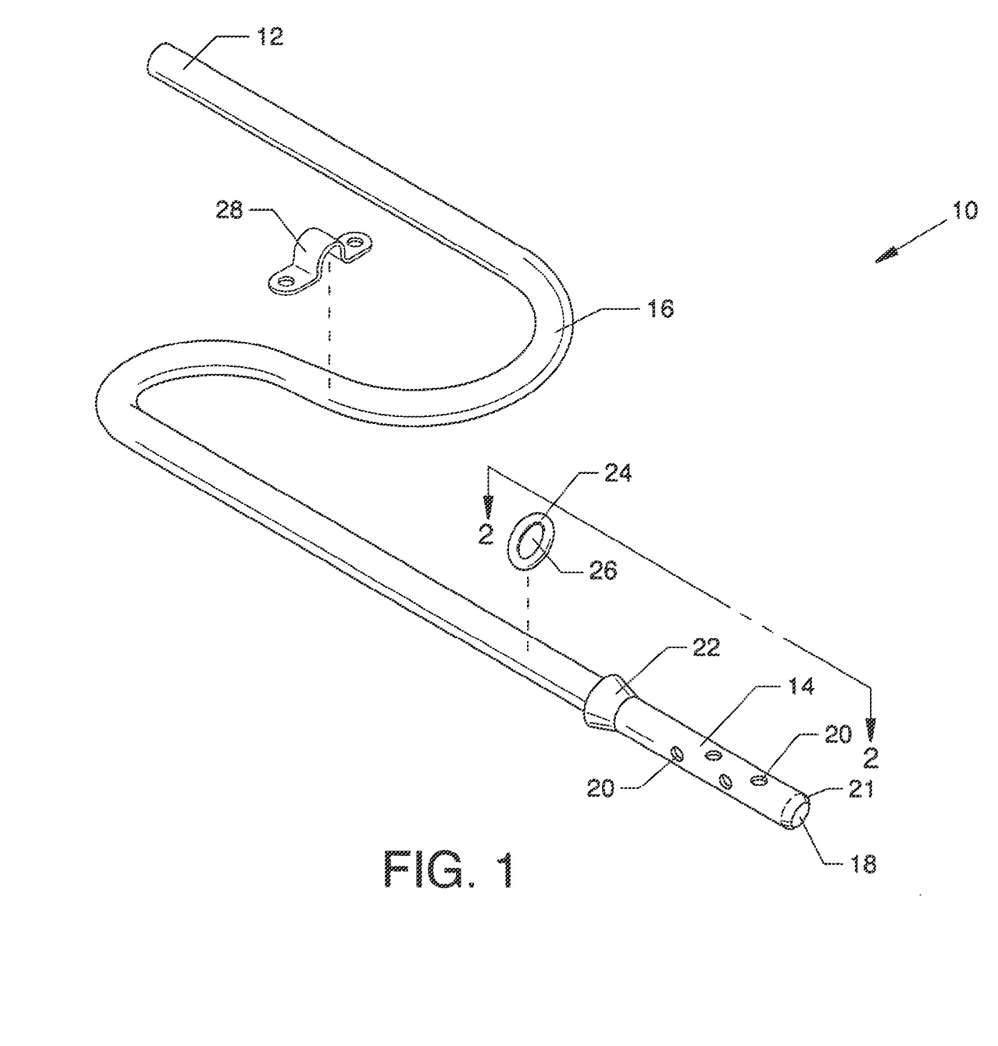
FIG. 1 is an isometric view of a shunt and associated components thereof, part of the present invention, which are used to equalize the translaminar pressure difference between the intraocular space and the intracranial space of the eye.

FIG. 1 is an isometric view of a shunt 10 and associated components thereof which are used to equalize the translaminar pressure difference between the intraocular space and the intracranial space of the eye. Preferably, the shunt 10 is flexible and fashioned of silicone or other suitable material. The flexible shunt 10 includes a proximal end 12, a distal end 14 and a midsection 16 extending generally between the proximal end 12 and the distal end 14. The flexible shunt 10 can be of a nonrestricted shape devoid of a memory shape or can have a memory shape (not shown) generally conforming to the shape of the human eye. A lumen 18 extends internally along the length of the shunt 10 between the proximal end 12 and the distal end 14 of the shunt 10. A plurality of like holes 20 communicating with the lumen 18 is distributed along, about, and through the wall of the distal end 14, Preferably, the tip 21 at the distal end 14 of the shunt 10 is rounded in order to prevent trauma and to aid in its insertion. A flexible conical anchoring barb 22 is located on the midsection 16 proximal to the plurality of holes 20 located in the distal end 14 in order to provide, in part, for affixing the distal end 14 of the shunt 10 in close proximity to a wound extending through the sclera of an eye. A flexible donut shaped anchoring ring 24 of silicone or other suitable material including a centrally located hole 26 is provided for coaxial placement along the midsection 16 in order to provide, in part, for affixing the distal end 14 of the shunt 10 in close proximity to a wound extending through the sclera of an eye. A U-shaped anchor 28 is provided for use in suture fastening the shunt 10 to the sclera of an eye. Preferably, the shunt 10 has an outer diameter of about 0.3 mm to about 1.0 mm, and most preferably, 0.5 mm. Preferably, the lumen 18 of the shunt 10 has an inner diameter of about 0.1 mm to about 0.5 mm, and most preferably, about 0.25 mm. A suitable length for the shunt 10 would be from 50 mm to about 100 mm and would be cut to the exact desired length by the surgeon at the time of surgery.

Figure 2:
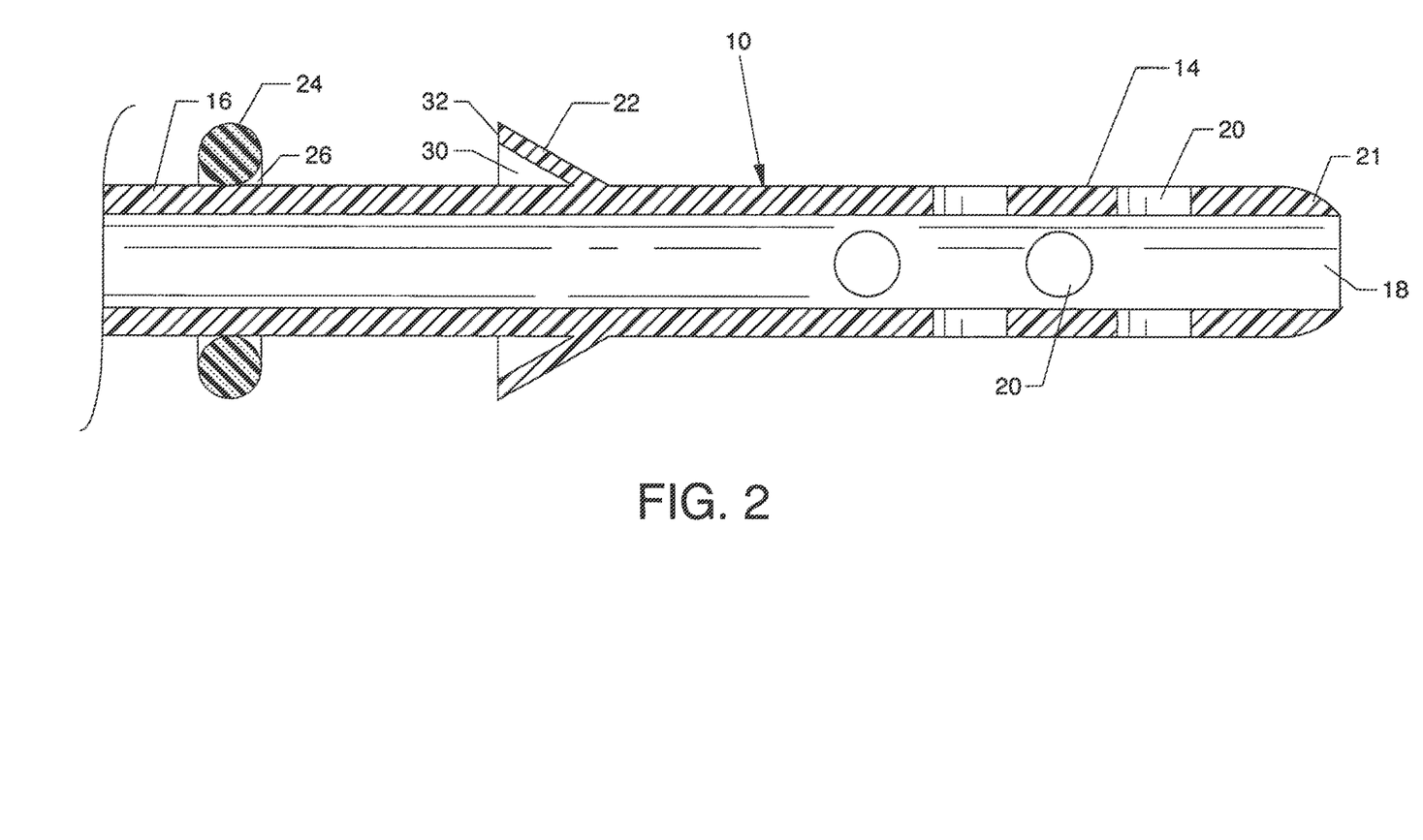
FIG. 2 is a cross section view of the distal end of the shunt along lines 2-2 of FIG. 1.
Figure 5:
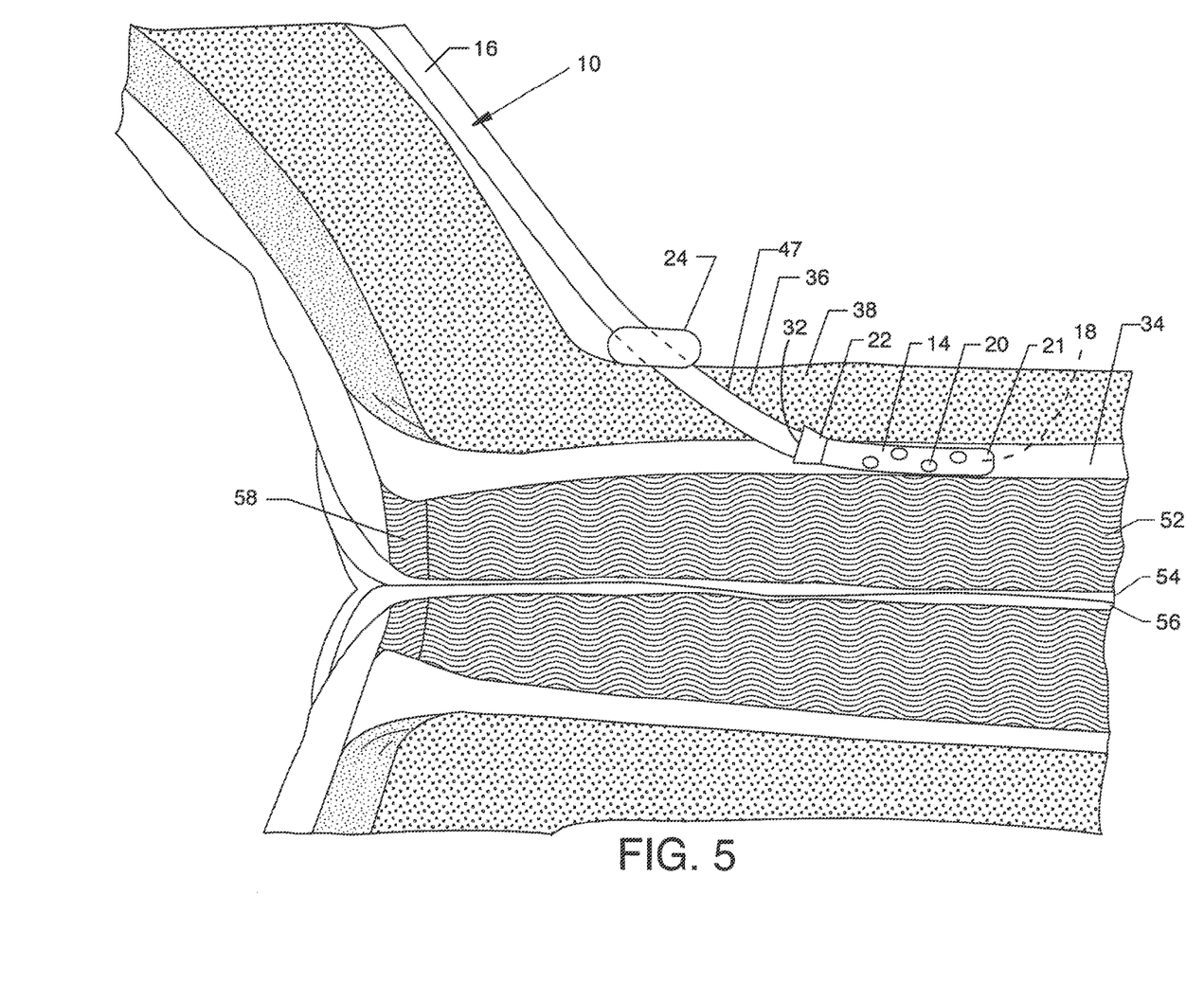

FIG. 2 is a cross section view of the distal end 14 of the shunt 10 including a portion of the midsection 16 along lines 2-2 of FIG. 1. Shown, in particular, is the plurality of holes 20 extending through the wall at the distal end 14 of the shunt 10 for communication of the lumen 18 with the exterior at the distal end 14 of the shunt 10. The plurality of holes 20 and the distal portion of the lumen 18 are aligned within and communicate with the subarachnoidal space 34, as shown in FIG. 5. Also shown is a cutback recess 30 and an arcuate edge 32 of the anchoring barb 22 which enables the anchoring of the shunt 10 to the dura mater 36 and the dural sheath 38, as shown later in detail in FIG. 5. The thickness of the anchoring barb 22 is reduced by the cutback recess 30 in order to provide flexibility of the anchoring barb 22.

Figure 3:
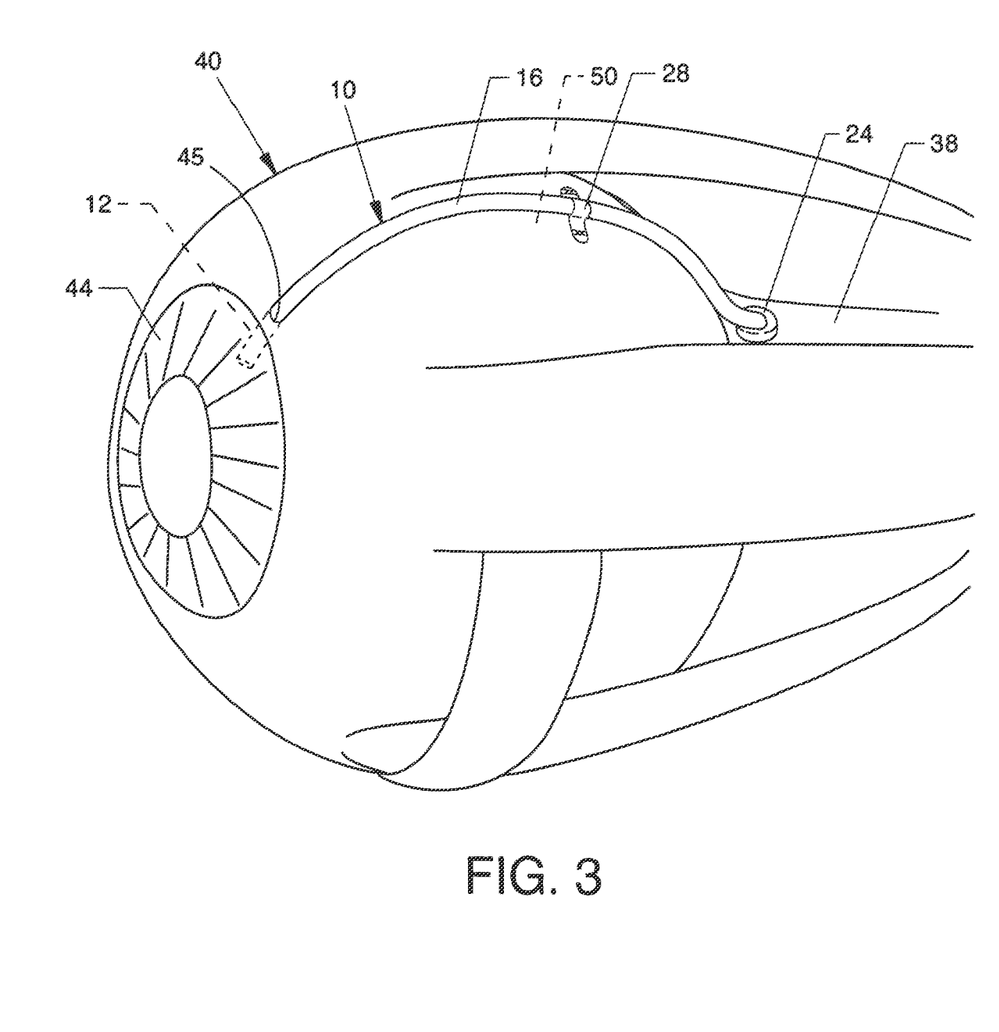
FIG. 3 is an isometric view showing the shunt attached to an eye.
Figure 4:
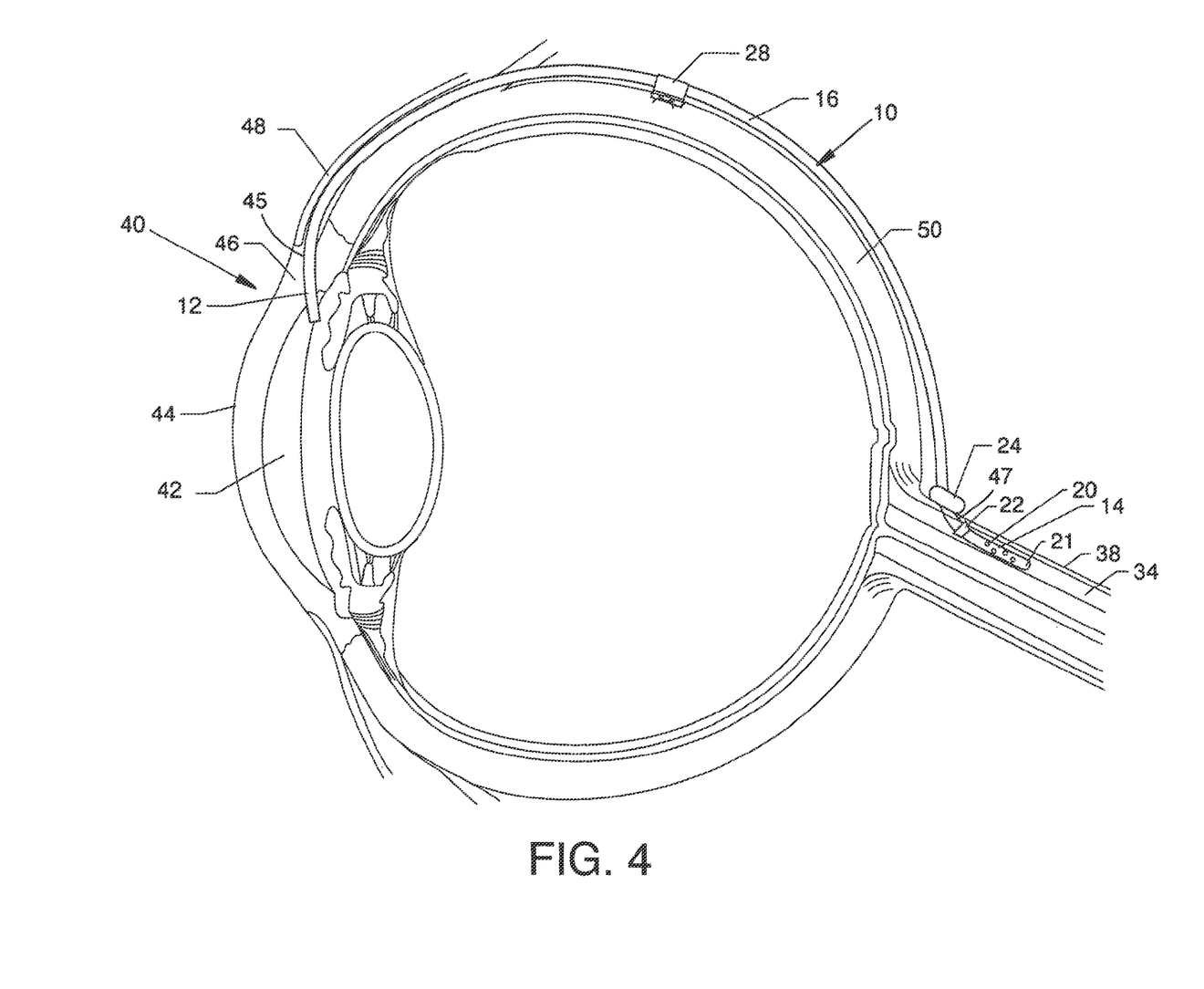
FIG. 4 is a cross section view showing the shunt attached to and in use with an eye; and, FIG. 5 is a cross section view showing the alignment of the distal end of the shunt extending through a wound in the dura mater and dural sheath and aligned within the subarachnoidal space.

FIG. 3 is an isometric view showing the shunt 10 attached to an eye 40. The proximal end 12 of the shunt 10 is inserted through a wound 45 in the limbus and extends a short distance behind the cornea 44 into the anterior chamber 42, as illustrated in FIG. 4. The midsection 16 of the shunt 10 is aligned with and follows the spherical or arcuate shape of the eye 40, i.e., the shunt 10 intimately contacts any layers exterior to the sclera 50 and is preferably secured, such as by the use of one or more anchors 28 aligned along the midsection 16 of the shunt 10, to the sclera such as by sutures, by a medical grade adhesive in use with an anchor 28, or by other suitable methods. In the alternative, a medical grade adhesive or another suitable method may be used to attach the shunt 10 to the eye 40 without the use of an anchor 28. As also shown in FIG. 5, the distal end 14 of the shunt 10 extends through the dura mater 36 and the dural sheath 38 and is secured therein, in part, by the use of the anchoring ring 24, or in the alternative, by a medical grade adhesive.

FIG. 4 is a cross section view showing the shunt 10 attached to and in use with an eye 40 and closely associated features thereof. Shown, in particular, is the routing of the shunt 10 from the proximal end 12 which enters through a wound 45 in the limbus 46 and aligns within and communicates with the anterior chamber 42, the midsection 16 which then traverses a short distance beneath the conjunctiva 48 and traverses about the exterior of the eye 40, the midsection 16 which continues traversing the exterior of the eye 40 and which is secured to the sclera 50 by one or more anchors 28, the distal end 14 secured by the anchoring ring 24 and the anchoring barb 22 to the dural sheath 38, and the distal end 14 which enters a wound 47 in the dural sheath 38 to align within and communicate with the subarachnoid space 34 within the structure of the dural sheath 38 (FIG. 5).

FIG. 5 is a cross section view showing the alignment at the distal end 14 of the shunt 10 having been extended through a wound 47 in the dura mater 36 and dural sheath 38 and aligned within the subarachnoidal space 34, as well as showing a portion of the midsection 16. The distal end 14 of the shunt 10 extends through and slidingly and flexibly frictionally engages the hole 26 of the anchoring ring 24 and is secured, in part, on the exterior of the dural sheath 38 in cooperation with the use of the flexible anchoring barb 22 which, in part, secures the distal end 14 of the shunt 10 within the subarachnoidal space 34, whereby a suitable portion of the edge 32 and the cutback recess 30 flexibly and anchoringly engage the dura mater 36 surrounding the subarachnoidal space 34. Also shown is the optic nerve bundle 52 located interior to the subarachnoidal space 34, the central retinal artery 54 and central retinal vein 56, respectively, and the lamina cribrosa 58 separating the intraocular space and the intracranial space. The subarachnoidal space 34 is in fluid communication with the intracranial space (not shown) and therefore intracranial pressure may be altered by the pressure flow through the shunt 10.

Mode of Operation

The shunt 10 is instrumental in modifying intracranial pressure, whereby the shunt 10 diverts aqueous humor fluid to the intracranial space via the subarachnoid space 34, thereby equalizing the translaminar pressure gradient, wherein the translaminar pressure difference (IOP–ICP) is beneficially less than the 6-10 mm Hg risk range; in fact, the translaminar pressure difference is equalized at zero. More specifically, aqueous humor fluid residing in the anterior chamber 42 can have an average intraocular pressure (IOP) of 16 mm Hg with a normal range of 10-21 mm Hg and the average intracranial pressure (ICP) can be about 12 mm Hg with a normal range of 5-20 mm Hg. The proximal end 12 of the shunt 10 which resides in the anterior chamber 42 and which communicates with the pressurized aqueous humor fluid residing in the anterior chamber 42 communicates such average intraocular pressure (IOP) of 16 mm Hg using the aqueous humor fluid medium along the lumen 18 of the shunt 10, whereby the relatively high pressure aqueous humor fluid can be urged along the lumen 18 and through the midsection 16 of the shunt 10 to communicate with the distributed holes 20 extending through the distal end 14 of the shunt 10 and with the extreme distal end of the lumen 18 in the shunt 10 where such holes and lumen end reside within the subarachnoidal space 34. The average intracranial pressure (ICP) of about 12 mm Hg is overridden by and is equalized with the average intraocular pressure (IOP) of 16 mm Hg at a value therebetween, but more importantly at a value which has no pressure differential across the lamina cribrosa 58, i.e., across the subarachnoid space 34 to the intracranial space. It is noted that such a pressure equalization also results in the beneficial raising of the intracranial pressure in order to treat or prevent glaucoma.

Various modifications can be made to the present invention without departing from the apparent scope thereof.

It is claimed:
1. A method of treating, inhibiting, or preventing damage to the optic nerve in an eye, the eye having a lamina cribrosa separating an intraocular space with an intraocular pressure (IOP) from an intracranial space with an intracranial pressure (ICP), the difference between IOP and ICP defined as translaminar pressure difference (TPD), the method comprising:
  receiving a patient, and
  reducing an indication of TPD magnitude in the eye of the received patient.

2. The method of claim 1, wherein receiving a patient includes receiving a patient with a symptom of optic nerve damage.

3. The method of claim 1, wherein receiving a patient includes receiving a patient to treat optic nerve damage.

4. The method of claim 1, wherein receiving a patient includes receiving a patient to inhibit optic nerve damage.

5. The method of claim 1, wherein receiving a patient includes receiving a patient to prevent optic nerve damage.

6. The method of claim 1, wherein reducing the indication of TPD magnitude in the eye of the patient includes increasing ICP in the patient.

7. The method of claim 6, wherein increasing ICP in the patient includes increasing ICP in the patient such that the indication of TPD magnitude is less than a threshold value.

8. The method of claim 7, wherein increasing ICP such that the indication of TPD magnitude is less than a threshold value includes increasing ICP such that the indication of TPD is less than a threshold value of about 10 mm Hg.

9. The method of claim 7, wherein increasing ICP such that the indication of TPD magnitude is less than a threshold value includes increasing ICP such that the indication of TPD is less than a threshold value of about 6 mm Hg.

10. The method of claim 7, wherein increasing ICP such that the indication of TPD magnitude is less than a threshold value includes increasing ICP such that the indication of TPD is about 0 mm Hg.

11. The method of claim 6, wherein increasing ICP in the patient includes non-surgically increasing ICP in the patient.

12. The method of claim 11, wherein non-surgically increasing ICP includes administering medication to increase ICP from a first ICP to a second ICP wherein the second ICP is greater than the first ICP.

13. The method of claim 12, wherein administering medication includes administering medication to stimulate cerebrospinal fluid (CSF) production in the patient.

14. The method of claim 12, wherein administering medication to stimulate CSF production in the patient includes administering medication to stimulate a choroid plexus of the patient.

15. The method of claim 12, wherein administering medication includes administering medication to inhibit cerebrospinal fluid (CSF) reabsorption in the patient.

16. The method of claim 1, comprising maintaining the reduced indication of TPD magnitude in the eye of the patient.

17. The method of claim 16, wherein maintaining the reduced indication of TPD magnitude includes maintaining the reduced indication of TPD magnitude at a threshold value less than about 10 mm Hg.

18. The method of claim 16, wherein maintaining the reduced indication of TPD magnitude includes maintaining the reduced indication of TPD magnitude at a threshold value less than about 6 mm Hg.

19. The method of claim 16, wherein maintaining the reduced indication of TPD magnitude includes maintaining the reduced indication of TPD magnitude at a threshold value of about 0 mm Hg.

* * * * *